US00PP33248P2

(12) United States Plant Patent
Doyle

(10) Patent No.: US PP33,248 P2
(45) Date of Patent: Jul. 13, 2021

(54) PEACH TREE NAMED 'W-2'

(50) Latin Name: *Prunus persica*
Varietal Denomination: W-2

(71) Applicant: James Doyle, Clovis, CA (US)

(72) Inventor: James Doyle, Clovis, CA (US)

( * ) Notice: Subject to any disclaimer, the term of this patent is extended or adjusted under 35 U.S.C. 154(b) by 0 days.

(21) Appl. No.: 16/880,526

(22) Filed: May 21, 2020

(51) Int. Cl.
*A01H 5/08* (2018.01)
*A01H 6/74* (2018.01)

(52) U.S. Cl.
USPC ..... Plt./196
CPC ..... *A01H 6/7463* (2018.05)

(58) Field of Classification Search
USPC ..... Plt./196
CPC ..... A01H 6/7463; A01H 5/08
See application file for complete search history.

*Primary Examiner* — Keith O. Robinson
(74) *Attorney, Agent, or Firm* — Marcus N. DiBuduo; John R. Aaron

(57) ABSTRACT

A new and distinct variety of peach tree (*Prunus persica*) named 'W-2', characterized by the white, melting type flesh and freestone pit of its fruit. The fruit is fine-textured and aromatic, with a rich and balanced mixture of acidity and sweetness. The fruit flesh has a moderate amount of red coloration and is firm, making the fruit very suitable for packing and shipping as a fresh market product. The fruit skin is durable and the color is a mix of red and white. The tree is of average stature and is precocious, productive and a regular bearer.

4 Drawing Sheets

Latin name: *Prunus persica.*
Variety denomination: 'W-2'.

BACKGROUND OF THE INVENTION

The present invention relates to a new and distinct cultivar of peach tree, botanically known as *Prunus persica* and hereinafter referred to by the variety denomination 'W-2'.

The 'W-2' white peach selection resulted from a controlled hybridization made in spring of 2011 by the Inventor in Roseville, Placer County, Calif. The breeding strategy for this specific cross was conceptualized by the Inventor in 2010.

The parentage of the 'W-2' peach selection is made up of two patented peach varieties—the female (seed) parent peach, 'Autumn Flame' (U.S. Plant Pat. No. 9,438, expired), and the male (pollen) parent peach, 'Snowflame' (U.S. Plant Pat. No. 5,251, expired). The flowers of the 'Autumn Flame' peach were emasculated in March of 2011 and pollen of the 'Snowflame' peach was collected and applied to the stigmas of 'Autumn Flame' on the same day. At maturity, in September of 2011, the ripe hybrid fruit of 'Autumn Flame' were harvested and the peach pits were cleaned, dried and stored. This population of hybrid seed was cracked out of the pits and stratified (given a cold treatment) in January of 2012. The cold treatment was completed by February of 2012 and the seeds were planted in containers. By the end of 2012, the hybrid seeds had grown and were large enough to furnish scion wood for the Inventor to graft onto four-year-old peach trees growing in a hedgerow in Roseville, Calif. This grafting was done by the Inventor in order to hasten the fruiting of the hybrid seedlings. The grafting occurred in spring of 2013 and the hybrid grafts first fruited in 2014. This individual seedling graft, identified as 'W-2', was selected for further evaluation in 2015. At the beginning of the 2017 growing season, the Inventor grafted one half of a mature peach-rooted tree (10+ years) growing in an orchard test plot controlled by the Inventor near the town of Sanger, Fresno County, Calif. A small amount of fruit developed on this test tree in 2018, followed by a large crop in 2019 at this test location. The new selection was propagated on a mature nectarine tree (10+ years old) growing on 'Nemaguard' peach rootstock (not patented) in spring of 2017. Propagules of the original 'W-2' seedling have shown that the unique features are stable and reproduced true to type.

SUMMARY OF THE INVENTION

The new peach selection, 'W-2', is a white-fleshed freestone peach with a moderate amount of red coloration in the flesh. The skin color is a mix of red and white. The tree is of average stature and is precocious, productive, and a regular bearer. The fruit skin is durable and the fruit flesh is firm, making the fruit very suitable for packing and shipping as a fresh market product. The fruit is fine-textured and aromatic, with a rich and balanced mixture of acidity and sweetness.

BRIEF DESCRIPTION OF THE PHOTOGRAPHS

The colors in the accompanying photographs are as nearly true as is reasonably possible in color photographs of this type. However, due to development, processing, printing, and reproduction, the leaves and fruit depicted herein may or may not be accurate when compared with the actual botanical specimens.

DETAILED BOTANICAL DESCRIPTION OF THE PLANT

Figure 1:
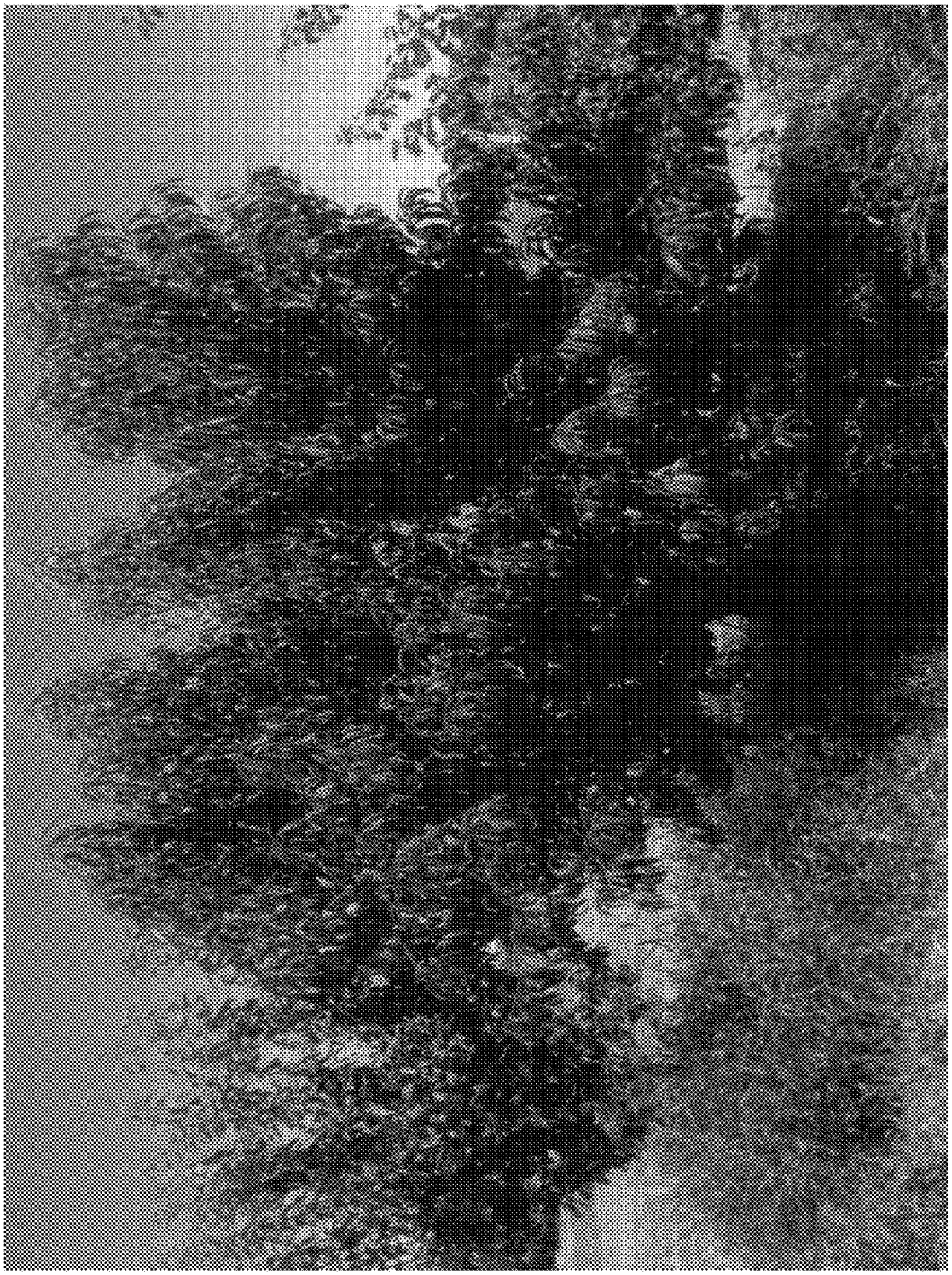
FIG. 1 is a photograph showing a peach tree of the new variety, comprising an approximately three year old scion growing on an approximately thirteen year old rootstock.
Figure 2:
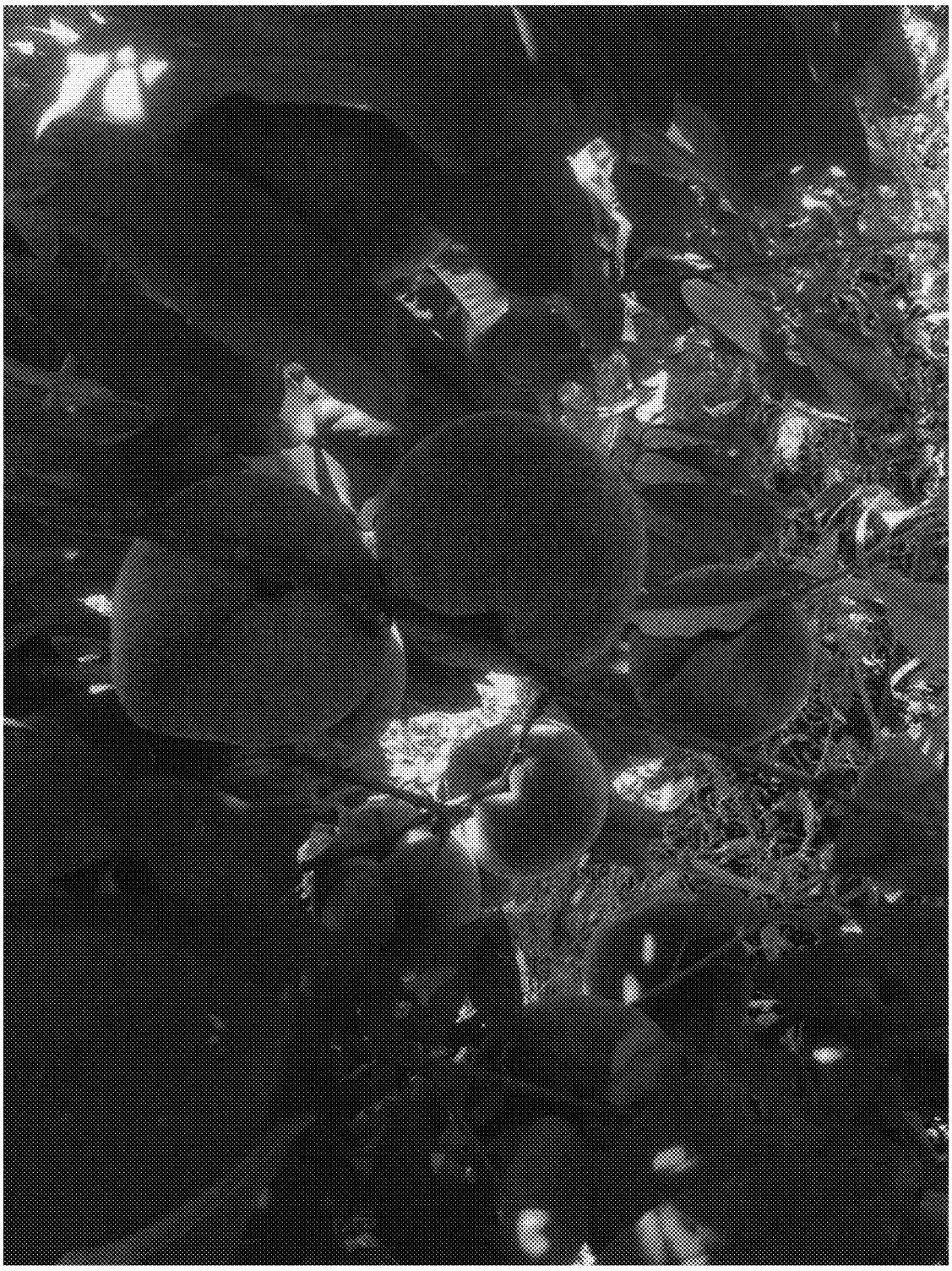
FIG. 2 is a photograph showing fruit on a peach tree of the new variety.
Figure 3:
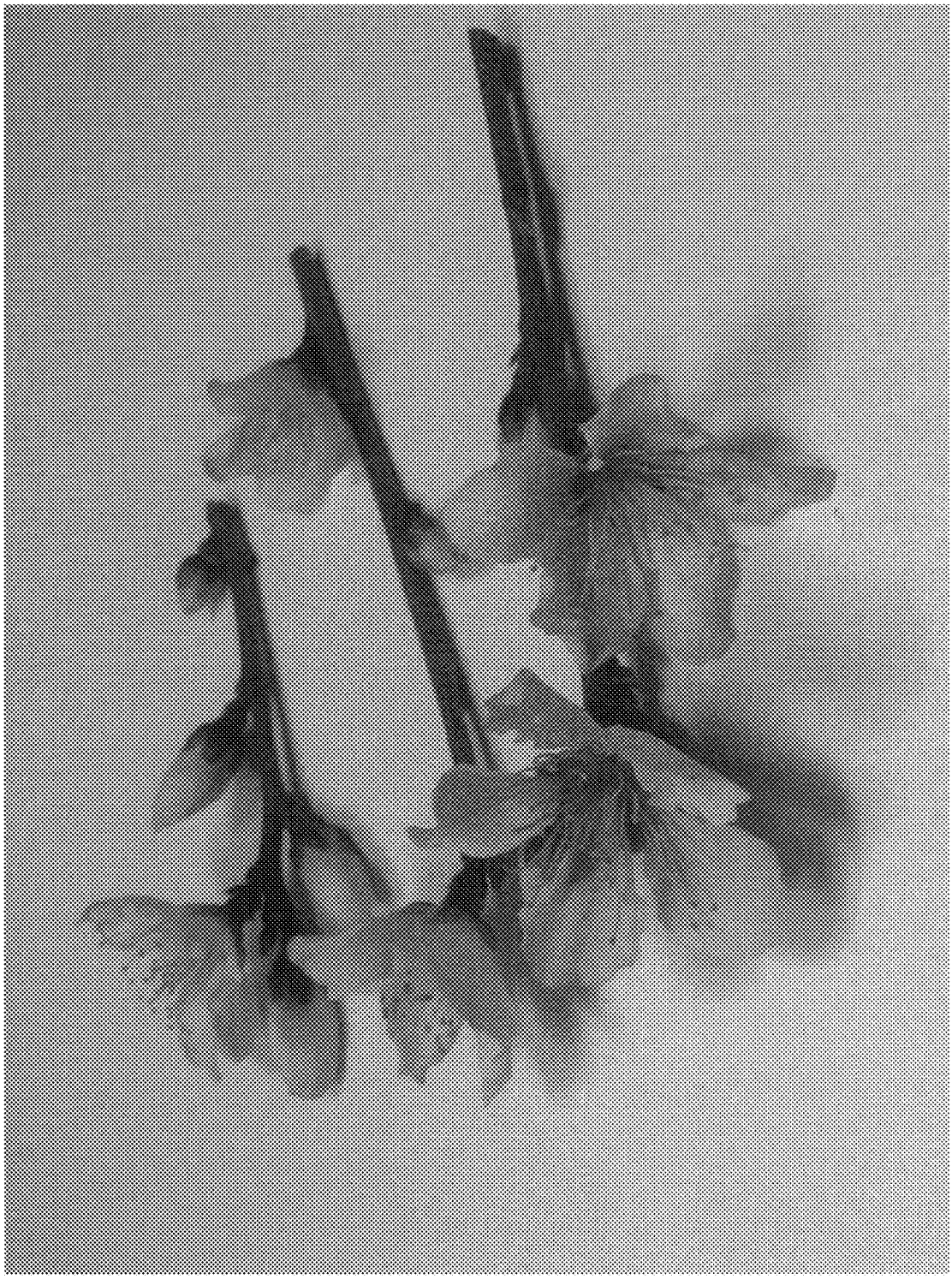
FIG. 3 is a photograph showing flowers of a peach tree of the new variety.
Figure 4:
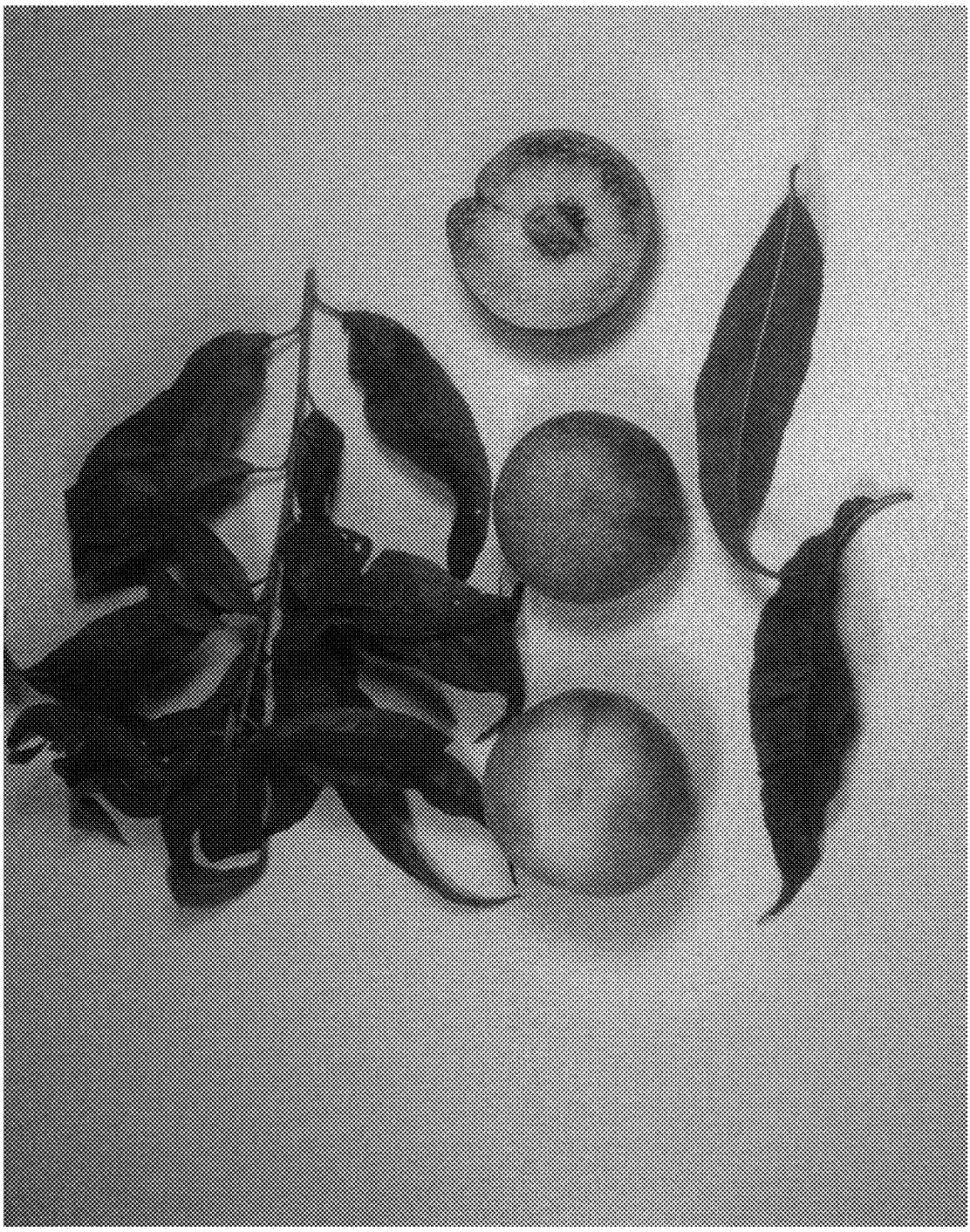
FIG. 4 is a photograph showing fruits and leaves of a peach tree of the new variety.

Fruit and plant material of the new white-fleshed peach selection, 'W-2', was obtained for description from a half-tree of the new peach growing at a test site controlled by the Inventor near the town of Sanger, Fresno County, Calif. This half-tree of the 'W-2' selection was grafted by the Inventor and is currently in its third growing season. Color definitions that are utilized in this description are from The "Royal Horticultural Society Colour Chart", 3rd edition, published at London, GBR in 1995, except where general color terms of ordinary dictionary significance are used.

Tree: The genus and species of this peach selection is *Prunus persica*. Tree size is about average for the species and the tree is relatively compact. The form of the tree is upright-spreading and it has been trained to an open-vase system. The tree height averages about 12.5 feet (3.8 meters) and tree width averages about 9.5 feet (2.9 meters). Row spacing is about 9.5 feet (2.9 meters) between trees and about 17 feet (5.2 meters) between rows. The tree produces from about 3.5 feet (1.1 meters) to about 4.0 feet (1.2 meters) of new growth in the top of the tree annually. In the Central Valley of California, the tree is vigorous, productive, hardy and produces a crop annually under typical environmental conditions.

*Trunk and scaffolds*.—The height of the two scaffolds, where the grafts were made, are about 2.3 feet and about 2.5 feet up, respectively, from the surface of the ground. The diameter of the two scaffolds, at the point of grafting, is about 12.3 cm and about 12.6 cm in width, respectively. There are a total of five scions of the 'W-2' peach placed on the two scaffolds.

*Secondary branches*.—The diameter of the upright secondary branches ranges from about 3.3 cm to about 4.5 cm in width at the base of the uprights. Bark texture on the upright secondaries is relatively rough, with a moderate amount of scarfskin. An average number of medium size bark lenticels are present throughout the surface of the bark. The lenticels range from about 2 mm to about 4 mm in width (horizontally) and from about 1 mm to about 2 mm in height. The lenticels are broadly oval in form. The bark surface is brownish in color, Fan 4-Sheet 177B. Smaller branches are of average thickness, and glabrous on the branch surface. The color of more mature branches varies from a dark yellow-green, Fan 3-Sheet 152A, to a more brownish color, Fan 4-Sheet 177B, especially when striations are present on the branch. Current season's growth displays a pale green-yellow color, Fan 3-Sheet 145A. The surface texture of these young shoots is also glabrous. Current season's growth, exposed to direct sunlight, often displays surface texture that is tinged with a reddish hue, Fan 4-Sheet 181A. Internode length on current growth is in the normal range, varying from about 13 mm to about 31 mm between nodes.

Leaves:

*Size and texture*.—The leaves are relatively large in size. Leaf measurements were taken from leaves growing at about mid-point on vigorously growing current season's upright shoots. Leaf length ranges from about 14.1 cm to about 19.2 cm. Leaf width ranges from about 3.7 cm to about 4.9 cm at its widest point. Leaf thickness is average for the species.

*Form*.—The general leaf form is lanceolate. The leaf tip is acuminate and the tip is often slightly reflexed downwards and slightly twisted sideways.

*Margins*.—The leaf margins are crenate in form, usually with low and uniform individual crenations. Most often, the crenations are tipped with a short, dark brown trichome. The leaf margins are usually only moderately undulate.

*Surface and vein color*.—Color of the upper leaf surface is a dark green, Fan 3-Sheet 137A. Color of the lower leaf surface is a lighter gray-green, Fan 3-Sheet 137D. On the underside of the leaf, the mid-vein is quite prominent and has a pale greenish-yellow color, Fan 2-Sheet 145C.

*Petioles*.—The leaf petioles are of medium length, ranging from about 11 mm to about 16 mm in length and averaging about 2.0 mm in width basally. Petiole color is a pale green, Fan 3-Sheet 147C, to slightly darker within the petiole groove.

*Glands*.—The leaf glands are medium to large in size, and most often reniform in shape, although at times a few globose form glands may be present. The number and location of the glands can be variable. From one to four glands can be present on the petiole, most often four. From one to five additional glands can be present on the basal margins of the leaf. Gland position is most frequently alternate, although glands located in opposite position are not uncommon. Young glands are a bright, shiny yellow-green in color, Fan 3-Sheet 154B, with the glands becoming darker and deteriorating with age.

*Stipules*.—The leaf stipules range from small to medium in size, varying from about 5.0 mm to about 7.0 mm in length. The stipules are linear lanceolate in form with deep serrate margins. The color of the stipule is a light green when young, Fan 3-Sheet 149B, becoming rusty-colored and brownish, Fan 4-Sheet 174B, as they deteriorate. The stipules are very early deciduous.

Flowers:

*Type*.—The floral type is rosette.

*Bloom timing*.—The bloom timing is average to slightly later in comparison to the bloom timing of most commercial peach varieties. The date of first bloom was approximately Feb. 26, 2020. The date of full bloom was approximately Mar. 6, 2020.

*Size*.—The flowers are large in size and showy in form. Average width of the flowers when fully expanded can range from about 30 mm to about 44 mm in diameter.

*Density*.—Floral density ranges from about 1 to 2 flowers per node, with one flower per node being most frequently present.

*Petals*.—The flower petals are usually five in number and most frequently ovate in form. Petal length can vary from about 17 mm to about 22 mm when fully expanded. Petal width varies from about 12 mm to about 14 mm. The petal claw is short, about 0.1 mm in length, moderately broad, about 0.1 mm in width, and truncate in form. Many petals are moderately to strongly cupped and rolled inwards. The petal margins are usually undulate, at times strongly so. The petal apices usually range from rounded to slightly domed in form. Petal color is pink, Fan 1-Sheet 56C, with darker pink coloration on the basal portion of the petal and, at times, along the petal margins, from Fan 1-Sheet 55C to Sheet 55B.

*Pedicel*.—The flower pedicel is quite short, averaging about 1.0 mm in length, and averaging about 1.0 mm to about 1.5 mm in thickness. The pedicel surface is glabrous. Pedicel color is a shiny yellow-green, Fan 3-Sheet 150B.

*Nectaries*.—The color of the floral nectaries is a pale greenish-yellow, Fan 1-Sheet 1C.

*Anthers*.—The anthers are plump and medium in size, from about 1.0 mm to about 1.5 mm in length. Anther color is a full light yellow, Fan 1-Sheet 11A. The position of the anthers is, generally, at about the same level as the stigma, but, occasionally, may be slightly above the stigma.

*Pollen*.—Pollen is abundant. Pollen color is a yellow-gold, Fan 1-Sheet 13A.

*Stamens*.—The stamens are variable in length, ranging from about 14 mm to as long as about 20 mm. Stamen filament color is variable, from almost white in young flowers, Fan 1-Sheet 155B, to a light pink, Fan 1-Sheet 36D, whereas in more mature flowers, the stamen color matures initially to a dark pink-red, Fan 1-Sheet 50C, and eventually to an even darker red-purple, Fan 2-Sheet 60D, when fully mature.

*Pistil*.—The floral pistil can range from about 17 mm to about 24 mm in length, including the ovary at the base. The ovary surface is highly pubescent, and the lower half of the style just above the ovary is also highly pubescent. The upper half of the style, just below the stigma, is less pubescent, becoming nearly glabrous at the attachment to the stigma. Pistil color is a pale green when young, Fan 3-Sheet 149D, but becomes slightly red-purple when fully mature, from Fan 2-70D, to a darker red-purple, Fan 2-Sheet 70C.

Fruit:

*Maturity*.—The fruit described below was in a firm ripe condition at full commercial maturity. Date of first pick was Aug. 4, 2019. Last crop pick was approximately Aug. 16, 2019.

*Size*.—The fruit size varies from medium to large. It is relatively uniform in shape. The fruit cheek diameter ranges from about 7.0 cm to about 7.7 cm in width. The suture diameter varies from about 7.2 cm to about 7.7 cm in width, and the axial diameter ranges from about 6.2 cm to about 6.7 cm in height. Fruit weight ranges from about 169 g to about 202 g.

*Form*.—Fruit form is variable in lateral aspect, from nearly globose, to slightly oblate, to slightly ovate. The fruit is also variable in apical aspect, from oval to nearly globose, with, at times, a raised ventral suture.

*Suture*.—The suture is a distinct, continuous line from base to apex, most distinct and prominent from midpoint down to the base, narrower from the midpoint up to the apex. The suture color ranges from a fairly intense red, Fan 1-Sheet 46A and 46B, through to a lighter red, Fan 1-Sheet 44D and is usually about the same intensity as the darkest red on the surrounding skin. Clefting can be present at times over the basal shoulder of the suture. Slight stitching on the suture area can also occasionally be present.

*Ventral surface*.—The ventral surface of the fruit can be irregular. At times, the fruit surface can be very smooth, or, at other times, it can have moderate lipping, typically more prominent on one half of the fruit.

*Stem cavity*.—The stem cavity is of moderate size. Cavity length varies from about 24 mm to about 30 mm, cavity width varies from about 20 mm to about 23 mm, and cavity depth varies from about 12 mm to about 15 mm. The cavity is oval in form. The ventral suture line is, at times, folded or occasionally clefted within the cavity basin. The fruit basal shoulders occasionally display an indentation where the fruit was pressed next to the bearing branch.

*Base*.—The fruit base is moderately truncate in form. The base angle can be slightly variable, but is usually at a right angle to the fruit axis.

*Apex*.—The fruit apex can be slightly variable. The pistil point is located within the suture groove, usually at a height even with the top of the fruit shoulders. A distinct depression is usually present on both the ventral and dorsal sides of the apex, located along the suture groove.

*Stem*.—The fruit stem is of average size, ranging from about 6.0 mm to about 8.0 mm in length and from about 3.0 mm to about 5.0 mm in thickness. Stem color is a pale yellow-green, Fan 3-Sheet 151C.

*Skin*.—The skin is of average thickness and the skin surface is moderately pubescent. The pubescence is very short and soft. Skin flavor is mild and almost neutral in acidity. The skin is tenacious to the flesh at commercial maturity. There has been no observed tendency for the skin to crack.

*Skin color*.—The skin coloration is mixed. The peach skin ground color can vary from a cream color, Fan 1-Sheet 6D, to a very light greenish-yellow, Fan 1-Sheet 1B. Although at times the ground color can be observed almost anywhere on the fruit, it is most frequently found around the basal end of the fruit and within the stem cavity. Red coloration occurs in several patterns on the fruit. Some red areas of the fruit skin are found in a washed pattern, while other areas are striped red or dappled red. The red color can range from a fairly intense red, Fan 1-Sheet 46A and 46B, through to a lighter red, Fan 1-Sheet 44D. Most striping and dapple marks are in the darker range. Within the fruit population on a tree of the 'W-2' selection, the red skin coloration can range from about 30% to about 90% of the fruit surface.

*Flesh color*.—The basic flesh color is white, Fan 4-Sheet 155D. Substantial red coloration can be present in the flesh, from about 20% to about 50% or more, of the interior surface area when a fruit is cut horizontally. The coloration is in the form of speckling, ranging from sparse to dense, and red colored rays extending from the fruit center outwards to the skin. The red color varies from a bright red, Fan 1-Sheet 45C, to a lighter red, Fan 1-Sheet 47C. The volume of red coloration often increases with advancing maturity.

*Flesh texture*.—The flesh texture is firm, fine textured and juicy at commercial maturity, becoming more juicy with advancing maturity.

*Ripening*.—The fruit ripens evenly.

*Flavor*.—The fruit flavor is a very high-quality blend of sweetness and acidity, both floral and aromatic.

*Aroma*.—The fruit aroma is strong and very pleasant.

*Eating quality*.—The fruit flavor is both sweet with moderate acidity, and is well-balanced. The eating quality is outstanding.

Stone:

*Attachment*.—The stone is a genetic freestone, but has many fibers attached to the stone throughout. Almost no air space is present between the stone and the fruit flesh.

*Size*.—The general stone size is medium. Stone length ranges from about 30 mm to about 35 mm, stone width varies from about 22 mm to about 26 mm, and stone thickness varies from about 17 mm to about 20 mm.

*Fibers*.—Many short tender fibers remain attached to the stone throughout, but most frequently along the lateral stone surfaces.

*Form*.—The stone form is somewhat variable. The form is most frequently oval, but can at times be slightly obovate.

*Base*.—The form of the stone base is usually truncate. The base angle can be either at a right angle to the stone axis or slightly oblique to the stone axis.

*Hilum*.—The hilum is of medium size and oval in form. Hilum length varies from about 3.5 mm to about 4.5 mm and hilum width varies from about 2.0 mm to about 3.0 mm. The hilum is surrounded by a distinct collar. The collar is raised and heavily grooved, and ranges from about 2 mm to about 3 mm in thickness.

*Apex*.—The apex form is generally acute, and is tipped with a short, acute and dentate tip.

*Sides*.—The stone sides are generally equal in size.

*Surface*.—The surfaces of the stone are usually quite rough. The lateral surfaces are heavily pitted with large irregular pits. Some deep grooves are present over the apical shoulders.

*Ventral edge*.—The ventral edge is moderately wide, from about 5 mm to about 7 mm when measured at mid-stone. Several low wings are present, usually coalesced at mid-stone and below, but converging apically. The wings are usually most prominent at about mid-stone, but less distinct and, at times, eroded basally.

*Dorsal edge*.—The dorsal edge has a deep groove from the stone base to above mid-stone. The main groove is less distinct over the apical shoulder and is at times heavily eroded in that area. The eroded area of the apical shoulder can be convex in shape. The basal to mid-portion of the dorsal edge groove is paralleled by two high ridges that are occasionally cut by cross-grooves.

*Color*.—Color of the stone is variable, from a light tan-brown, Fan 4-Sheet 164D, to a light brown, Fan 4-Sheet 165C, and with some lateral areas of the stone displaying an even darker brown, Fan 4-Sheet 177B. A moderate amount of reddish, Fan 2-Sheet 58A, staining can be present on the stone surface, more apparent basally.

*Tendency to split*.—No tendency for the stone to split has been observed.

*Resistance and susceptibility to pests and/or diseases*.—The present variety has not been tested for resistance and/or susceptibility to any pests or diseases.

COMPARISONS WITH THE PARENT PLANTS

The present variety can be compared to two commercial peach varieties, both of which make up the parentage of the present variety. The 'Autumn Flame' peach is the female (seed) parent of present variety. The 'Autumn Flame' peach is a widely planted commercial peach variety and is substantially different than the present variety. The 'Autumn Flame' peach is a yellow-fleshed peach, in contrast to the flesh of the 'W-2' peach that is white. The white-fleshed 'Snowflame' peach is the male (pollen) parent of the present variety. A principal difference between the 'Snowflame' peach and the present variety is that the 'Snowflame' peach is a clingstone peach with non-melting type flesh, while the 'W-2' peach has a freestone pit with melting type flesh.

What is claimed is:

1. A new and distinct cultivar of *Prunus persica* tree named 'W-2', substantially as illustrated and described herein.

* * * * *